United States Patent [19]

Pytlewski et al.

[11] Patent Number: 4,523,043

[45] Date of Patent: * Jun. 11, 1985

[54] REAGENT AND METHOD FOR DECOMPOSING ORGANOSULFUR COMPOUNDS

[75] Inventors: Louis L. Pytlewski; Kenneth Krevitz, both of Philadelphia, Pa.; Arthur B. Smith, Newark, Del.

[73] Assignee: The Franklin Institute, Philadelphia, Pa.

[*] Notice: The portion of the term of this patent subsequent to Jun. 29, 1999 has been disclaimed.

[21] Appl. No.: 571,845

[22] Filed: Jan. 18, 1984

Related U.S. Application Data

[60] Continuation-in-part of Ser. No. 386,945, Jun. 10, 1982, abandoned, which is a division of Ser. No. 158,359, Jun. 11, 1980, Pat. No. 4,337,368, which is a continuation-in-part of Ser. No. 142,865, Apr. 21, 1980, abandoned.

[51] Int. Cl.$^3$ .................. C07C 29/00; C07C 31/08
[52] U.S. Cl. ......................... 568/840; 423/561 A; 568/910; 568/915; 568/920
[58] Field of Search .................. 423/561 A; 568/910, 568/915, 920, 840

[56] References Cited

U.S. PATENT DOCUMENTS

| | | | |
|---|---|---|---|
| 2,837,573 | 6/1958 | Mavity | 568/840 |
| 3,239,568 | 3/1966 | De Pree et al. | 568/840 |
| 3,459,813 | 8/1969 | Dombro | 568/840 |
| 3,483,993 | 12/1969 | Dombro | 568/840 |
| 3,515,759 | 6/1970 | Dombro | 568/840 |
| 3,544,639 | 12/1970 | Bloch | 568/840 |
| 3,551,504 | 12/1970 | Schmerling et al. | 568/840 |
| 3,557,221 | 1/1971 | O'Connor et al. | 568/840 |
| 3,615,191 | 10/1971 | Bach et al. | 423/561 A |
| 4,337,368 | 6/1982 | Pytlewski et al. | 568/730 |

OTHER PUBLICATIONS

Billheimer et al., "J. Am. Chem. Soc.", vol. 52, (1930), pp. 4338-4344.

*Primary Examiner*—J. E. Evans
*Attorney, Agent, or Firm*—Dann, Dorfman, Herrell and Skillman

[57] ABSTRACT

Organosulfur compounds containing a C-S bond are decomposed by reaction with a reagent made from an alkali metal, a polyglycol or a monoalkyl ether thereof and oxygen, which effects decomposition by cleavage of the C-S bond.

9 Claims, No Drawings

REAGENT AND METHOD FOR DECOMPOSING ORGANOSULFUR COMPOUNDS

This application is a continuation-in-part of application Ser. No. 386,945, filed June 10, 1982, now abandoned, which is a division of application Ser. No. 158,359, filed June 11, 1980, now U.S. Pat. No. 4,337,368 which, in turn, is a continuation-in-part of application Ser. No. 142,865, filed Apr. 21, 1980, now abandoned, all in the names of Louis L. Pytlewski, Kenneth Krevitz and Arthur B. Smith.

BACKGROUND OF THE INVENTION

The present invention relates to a process for decomposing organosulfur compounds in an efficient and effective manner using a decomposition reagent made from readily available and a relatively inexpensive starting materials.

During the past several years, there has been developed at the Franklin Research Center of the Franklin Institute, Philadelphia, Pa., a reagent and method for stripping the halogen substituents from various halogenated organic compounds, including PCBs, thus rendering them non-toxic and readily disposable. More specifically, Pytlewski, Krevitz and Smith, in their U.S. patent application Ser. No. 158,359, filed June 11, 1980, now U.S. Pat. No. 4,337,368, describe and claim a method for the decomposition of toxic halogenated organic substances, by treating the toxic substances with a reagent formed from the reaction between an alkali metal, a liquid reactant, such a polyglycol or a polyglycol monoalkyl ether, and oxygen, This reagent, commonly referred to as NaPEG reagent, or simply NaPEG, produces substantially complete dehalogenation simply by mixing it with the halogenated substance under ambient conditions.

SUMMARY OF THE INVENTION

In accordance with the present invention, it has been found that in addition to its utility in dehalogenating halogenated organic substances, NaPEG reagent is useful for the decomposition of various organosulfur compounds containing at least one C-S bond. In carrying out the present invention, the decomposition reagent is made by reacting an alkali metal, a suitable liquid reactant, such as a polyglycol or a polyglycol monoalkyl ether, and oxygen to form the decomposition reagent, and adding the organosulfur compound, or a mixture of such compounds to the decomposition reagent in the presence of oxygen to cleave any C-S bonds present therein, and thereby decompose the organosulfur compound.

The present invention provides a practical and effective way of decomposing organosulfur compounds in relatively concentrated form, and may be particularly useful for the disposal of certain chemical and biological warfare agents. The present invention may also be used for the removal of organosulfur compounds present as contaminants in other materials, e.g. in the desulfurization of petroleum products, such as motor fuels. Industrial effluent streams may also be treated in accordance with the present invention for the removal of toxic or malodorous organosulfur compounds. Furthermore, the present invention is at once capable of decomposing organosulfur compounds and producing useful products which are easily recoverable from the decomposition reaction mixture.

DESCRIPTION OF THE INVENTION

As a practical matter, the alkali metals particularly suitable for practicing the present invention are sodium, lithium and potassium or the amalgams of these metals. Of these, sodium is preferred because of its high reactivity and relatively low cost.

The liquid reactants that may be utilized in carrying out the present invention, have the general formula:

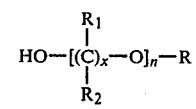

wherein R is hydrogen or lower alkly, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400, and x has a value of at least 2, which formula includes polyglycols and polyglycol monoalkyl ethers. The lower alkyl radical in the foregoing formula may be methyl, ethyl, propyl, butyl, isobutyl, etc. The cycloalkyl radical may be cyclopentyl, cyclohexyl, cycloheptyl and cyclooctyl. The aryl radical may be phenyl, benzyl, biphenyl, naphthyl, etc. The substituents on the $R_1$ and $R_2$ radicals include, but are not limited to lower alkyl, e.g. methyl, ethyl, propyl, butyl, isobutyl, etc.; halo, e.g., chloro, bromo; nitro; sulfato; carboxyl; amino; mono- and di-lower-alkylamino, e.g. methylamino, ethylamino, dimethylamino, methylethylamino; amido; hydroxy, lower alkoxy, e.g. methoxy, ethoxy, etc.

Suitable liquid reactants falling within the above formula include diethylene glycol, diethylene glycol monomethyl ether, polyether glycols, such as polyethylene glycols, polypropylene glycols, and polybutylene glycol and related long chain glycol monoalkyl ethers. The preferred liquid reactants are those of the above general formula wherein $R_1$ and $R_2$ are hydrogen and x is 2. Particularly preferred are polymers of polyethylene glycol having the formula $HO[CH_2-CH_2-O]_nH$ wherein n may have a value between about 2 and about 400. These polymers have an average molecular weight range from about 100 to about 20,000. Neither low volatility, non-polar liquids, nor glycolic liquids in which both terminal hydroxyl groups are alkylated has been found to produce the desired decomposition.

The term "polyglycols", as used herein, is intended to signify polymers of dihydric alcohols.

Oxygen is a necessary reactant in the formation of the decomposition reagent. When the reaction is carried out in a vessel open to the air, for example, the alkali metal and the liquid react vigorously with the evolution of hydrogen gas. Formation of the reagent is indicated by the reaction mixture changing from relatively clear to deep amber in color. This color change is distinct and readily observable. Alternatively, the decomposition reagent may be prepared by reacting sodium and polyethylene glycol in an inert atmosphere, e.g. one consisting essentially of nitrogen, with oxygen being thereafter introduced into the resultant solution, whereupon the decomposition reagent will be formed, as indicated by the aforementioned color change. The two-step procedure just described has the advantage over the one-step procedure that it avoids having hydrogen and oxygen present simultaneously in the reaction system, thereby avoiding a potential explosion hazard. Furthermore, it lessens the possibility that inactive by-product will be formed.

In preparing the decomposition reagent, the alkali metal and liquid reactant are simply mixed together in a vessel open to the air, preferably with stirring. The reaction generally proceeds at ambient temperature, but may be heated to accelerate the rate of reaction. The extent of heating required will vary depending on the particular metal and liquid reactant used. In the case of a decomposition reagent formed from sodium and a polyethylene glycol having an average molecular weight of 400, for example, heating of the mixture to a temperature in the range of about 50° C. to about 80° C. gives a satisfactory reaction rate. Upon heating, the reaction becomes exothermic and the temperature of the reaction mixture rises to near or above the melting point of the sodium, which is 97.6° C. With the rise in temperature, the sodium becomes molten and reaction with the liquid ensues. Alkali metals having lower melting points may undergo reaction with the liquid after initial mixing at room temperature.

Theoretically, the stoichiometry of the reaction requires one mole of alkali metal per mole of polyglycol or polyglycol monoalkyl ether. In practice, however, it has been found that satisfactory results are obtained using a slight molar excess of the alkali metal or alkali metal hydroxide, i.e., on the order of 1 to 2 moles of alkali metal per mole of polyglycol or polyglycol monoalkyl ether. Particularly good results are obtained when the mole ratio of these two reactants is 1.1 to 1. It appears that at this particular mole ratio, optimum solubility of the alkali metal in the polyglycol or polyglycol monoalkyl ether is achieved.

Formation of the reagent does not require a solvent. Nor is a solvent needed for miscibility or reactivity of the reagent with organosulfur compounds. Reagent formed in accordance with the present invention is useful without a solvent because it is liquid at normal reaction temperatures, e.g., 20° C. to 125° C. Alkali metal hydroxides and alkoxides which have been proposed heretofore for various reactions with relatively non-polar organic substances, on the other hand, require dissolution in polar, usually protic solvents, such as alcohols. By comparison to such solutions, the reagents of the present invention may be prepared substantially unsolvated and used as such. In other words, the decomposition reagent used in the practice of the present invention may be formed as a homogeneous material, useful as is, in effect providing its own solvent.

If desired, the reagent of the present invention may be prepared using a solvent. It has been found, however, that solvation of the reagent tends to reduce its reactivity. The reduction in reactivity is generally greater for polar protic solvents than it is for polar aprotic solvents.

Reagent formed from an alkali metal, a polyglycol or polyglycol monoalkyl ether of the above formula and oxygen, in the manner described above, is believed to be a complex of the crown ether variety, with the residue of the polyglycol or polyglycol monoalkyl ether compound encircling an alkali metal ion. Such complexes contain at least one basic, neucleophilic anion and at least one superoxide radical. The nucleophilic anion is believed to be an alkoxide ($RO^-$) or a hydroxide ($ROH.OH^-$), where R signifies a polyglycol or polyglycol monoalkyl ether residue. These are ideal moieties for complexation with metal cations. The presence of nucleophilic anion in the reagent may be determined by infra-red analysis. Infra-red spectra of the reagent described hereinabove exhibit no maxima of OH stretch absorption bands above 3000 $cm^{-1}$, as normally appears in the spectra of primary alcohols, such as polyglycols. Rather, the OH stretch adsorption bands of the reagent appear at much lower wave numbers, which is indicative of very strong hydrogen bonding in the reagent. This shift is believed to be attributable to the presence of the basic nucleophilic anion in the reagent. As a result of this shift, the intensity of the OH stretch absorption band is appreciably decreased to the point that it appears as a shoulder of the CH stretch absorption band, which generally occurs at about 2900 $cm^{-1}$. In this respect the decomposition reagent used in the present invention is distinguishable from a simple alkali metal alcoholoate.

The presence of the superoxide radical in the reagent is determined by the occurence of a strong electron spin resonance (E.S.R.) absorption band located at approximately 3,300 gauss, having a narrow band width of about 7 gauss. This E.S.R. spectrum matches that observed for the superoxide ion, $O_2^-$.

Once formed, the decomposition reagent may be used immediately, or it may be stored for later use. In general, the reagent may be stored for at least six months without appreciably diminishing its reactivity.

In order to achieve decomposition of an organosulfur compound in accordance with this invention, all that is necessary is to add the organosulfur compound to the reagent in the presence of oxygen. While decomposition will generally occur at ambient temperature, the mixture may be heated to speed the rate of reaction. Heating to a temperature in the range of about 40° C. to about 180° C. has been found to produce satisfactory results. Of course, the temperature may vary depending upon the particular decomposition reagent used and the organosulfur compound sought to be decomposed.

The order in which the steps of the decomposition method are carried out is not considered critical. While a presently preferred procedure has been described hereinabove, the method may be practiced otherwise. For example, the organosulfur compound may be added to the polyglycol or polyglycol monoalkyl ether prior to the addition of the alkali metal, or the latter may be added together with the organosulfur compound to the polyglycol or polyglycol monoalkyl ether. If desired, the alkali metal may be mixed with the organosulfur compound, and the polyglycol or polyglycol monoalkyl ether added later to the resultant mixture. As another alternative, the alkali metal and organosulfur compound may be added to the polyglycol or polyglycol monoalkyl ether in an oxygen-free atmosphere, e.g., pure nitrogen, with subsequent introduction of oxygen into the reaction mixture to effect rapid decomposition of the organosulfur compound.

Standard safety precautions used in the handling of alkali metals should be followed in preparing and using the reagent.

Decomposition of organosulfur compounds using the method of the present invention produces relatively innocuous products, the principal ones being sodium sulfide and various useable oxygenated derivatives of the organosulfur compounds, including alcohols and glycols, which may either be disposed of under environmentally safe conditions, or recovered from the reaction mixture by conventional separation techniques.

The following examples further describe the manner and process of making and using the present invention, but are not intended to limit the invention.

EXAMPLE I

Preparation of Decomposition Reagent

NaPEG was prepared by placing 900 ml. of polyethylene glycol, having an average M.W. of 400 (referred to in these examples as PEG 400) in a 3000 ml. beaker and heating until the temperature approached 80° C. Stirring was accomplished by using an efficient overhead mechanical stirrer. Thereafter, approximately 55 grams of freshly cut sodium metal was added within a two minute period, in order to reduce the possibility of a sodium fire.

Within ten minutes, the temperature of the mixture rose to about 120° C. and was maintained as close as possible to this value, until all the sodium, which melted and formed a shiny layer on top of the solvent, had reacted. Reaction is evidenced by the change of color of the PEG 400 to a dark amber and the disappearance of the shiny metal layer. If all of the sodium does not react, small additions of PEG 400 may be used to effect complete reaction. Alternatively, the NaPEG mixture may be placed in a separatory funnel and the lower NaPEG layer drawn off. The unreacted sodium metal rises to the top and may be decomposed by reaction with methanol.

EXAMPLE II

Alternate Preparation of Decomposition Reagent

NaPEG reagent was also prepared in accordance with the following two-step procedure. In the first step, 900 ml. of PEG 400 and 55 grams of sodium were placed in a three-neck round bottom flask (2000 ml.), which was continually flushed with nitrogen gas and heated to a temperature of 80° C. Stirring was accomplished by using an efficient overhead mechanical stirrer. Since no oxygen was present in the reaction vessel, the possibility of a sodium fire was greatly reduced. Hydrogen was evolved as a result of the reaction between the dissolved sodium and the PEG 400. At this point, the reaction mixture was essentially colorless. When air was introduced into the reaction mixture, a rapid reaction occurred as evidenced by the color change to dark amber as described in Example I, thus indicating that the NaPEG reagent had been formed.

EXAMPLE III

A 5 ml. sample of neat chloroethylethyl-sulfide (a "Mustard gas" model compound) was added to 25 g. of NaPEG reagent which was prepared according to Example I, above, and heated to 100° C. The reaction mixture was analyzed and the products were determined to be Na$_2$S, NaCl and ethanol. This example demonstrates that the present invention is effective for decomposing organosulfur compounds containing a C-S bond by cleavage of the C-S bond.

While a presently preferred embodiment of this invention has been described hereinabove, it is not intended to limit the invention to such embodiment, but various modifications may be made therein and thereto without departing from the spirit and scope of the invention, as set forth in the following claims.

What is claimed is:

1. A process for the decomposition of an organosulfur compound containing a C-S bond, comprising the steps of:
    (a) providing a decomposition reagent formed by reacting an alkali metal, a reactant having the general formula:

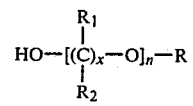

wherein R is hydrogen or lower alkyl, R$_1$ and R$_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400 and x has a value of at least 2, and oxygen; and
    (b) reacting said decomposition reagent with said organosulfur compound in the presence of oxygen to effect cleavage of said C-S bond, thereby decomposing said organosulfur compound.

2. A process as claimed in claim 1, wherein said decomposition reagent is produced from an alkali metal selected from the group consisting of sodium, potassium, and amalgams thereof, and a liquid reactant of the above general formula wherein R$_1$ and R$_2$ are hydrogen, x is 2, and n has a value between 3 and 400.

3. A process for the decomposition of an organosulfur compound containing a C-S bond, comprising the steps of:
    (a) providing a reaction mixture comprising said organosulfur compound, a reactant having the general formula:

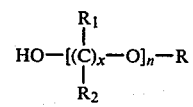

wherein R is hydrogen or lower alkyl, R$_1$ and R$_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value of from 2 to about 400, and x has a value of at least 2, and an alkali metal; and
    (b) reacting said reactant with said alkali metal and oxygen to form a decomposition reagent, which effects cleavage of said C-S bond, thereby decomposing said organosulfur compound.

4. A process as claimed in claim 3, wherein the alkali metal is selected from the group consisting of sodium, potassium, and amalgams thereof, and R$_1$ and R$_2$ in the general formula are hydrogen, x is 2, and n has value between 3 and 400.

5. A process for the decomposition of an organosulfur compound containing a C-S bond compound, comprising the steps of:
    (a) providing a reaction mixture comprising said organosulfur compound, a reactant having the general formula:

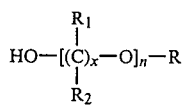

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value of from 2 to about 400, and x has a value of at least 2, and an alkali metal;

(b) reacting said reactant with said alkali metal in a substantially oxygen-free atmosphere to produce an intermediate product; and (c) reacting oxygen with the intermediate product produced in step b to form a decomposition reagent which effects cleavage of said C-S bond, thereby decomposing said organosulfur compound.

6. A process as claimed in claim 5, wherein the substantially oxygen-free atmosphere consists essentially of nitrogen.

7. A process as claimed in claim 5, wherein the alkali metal is selected from the group consisting of sodium, potassium, and amalgams thereof, and $R_1$ and $R_2$ in the general formula are hydrogen, x is 2, and n has a value between 3 and 400.

8. A process for decomposition of an organosulfur compound comprising the steps of:

(a) reacting sodium, polyethylene glycol and oxygen at a temperature of from about 80° C. to about 120° C. to form a decomposition reagent; and (b) adding the organosulfur compound to the decomposition reagent in the presence of oxygen and heating to about 100° C. to effect cleavage of said C-S bond, thereby decomposing said organosulfur compound.

9. A process as claimed in claim 8, wherein the organosulfur compound is chloroethylethylsulfide.

* * * * *